United States Patent [19]

Peindl et al.

[11] Patent Number: 5,662,591
[45] Date of Patent: Sep. 2, 1997

[54] APPARATUS FOR EXERCISING AND MEASURING STRENGTH OF A PATIENT'S LIMB AND AN ADJUSTABLE PIVOT CLAMP

[75] Inventors: Richard D. Peindl, Charlotte, N.C.; Melissa Lee McCarthy; Ellen Jane MacKenzie, both of Baltimore, Md.

[73] Assignees: The Johns Hopkins University, Baltimore, Md.; The Charlotte-Mecklenburg Hospital Authority, Charlotte, N.C.

[21] Appl. No.: 451,173

[22] Filed: May 26, 1995

[51] Int. Cl.$^6$ .................................. A61B 5/103
[52] U.S. Cl. .................. 601/24; 601/33; 128/774; 5/648; 73/379.01
[58] Field of Search ................... 128/774; 601/23, 601/24, 33–35; 73/379.01; 482/137, 142, 909; 248/222.52, 286.1, 287.1, 298.1; 5/601, 621, 623, 624, 646, 648

[56] References Cited

U.S. PATENT DOCUMENTS

| | | |
|---|---|---|
| 1,398,092 | 11/1921 | Drake . |
| 1,792,612 | 2/1931 | Staley . |
| 2,340,572 | 2/1944 | Smith ................................ 248/287.1 |
| 2,446,470 | 8/1948 | Godwin . |
| 2,855,199 | 10/1958 | Noland et al. . |
| 3,120,954 | 2/1964 | Apostol ................................ 482/137 |
| 3,285,070 | 11/1966 | McDonough ..................... 73/379.01 |
| 3,339,913 | 9/1967 | Anderson ........................... 248/298.1 |
| 3,374,675 | 3/1968 | Keropian . |
| 3,612,042 | 10/1971 | Fry . |
| 3,904,195 | 9/1975 | Chavanne . |
| 3,970,274 | 7/1976 | Resk . |
| 4,307,608 | 12/1981 | Useldinger et al. ............. 73/379.01 |
| 4,368,957 | 1/1983 | Shemtov ........................... 248/286.1 |
| 4,549,555 | 10/1985 | Fraser et al. . |
| 4,551,872 | 11/1985 | Reed . |
| 4,602,618 | 7/1986 | Berzé . |
| 4,763,897 | 8/1988 | Yakata ................................ 482/137 |
| 4,772,015 | 9/1988 | Carlson et al. .................... 482/92 |
| 4,930,523 | 6/1990 | Laico et al. . |
| 5,078,152 | 1/1992 | Bond et al. . |
| 5,090,421 | 2/1992 | Wagner, III ..................... 73/379.01 |
| 5,265,589 | 11/1993 | Wang . |
| 5,476,241 | 12/1995 | Helman ............................ 248/286.1 |

OTHER PUBLICATIONS

*Knee Extension Torque in Stroke Patients: Comparison of Measurements Obtained With a Hand–Held and a Cybex Dynamometer,* R. W. Bohannon, Physiotherapy Canada, Nov./Dec., vol. 42, No. 6, pp. 284–287.

*A Static Dynamometer Measuring Multidirectional Torques Exerted Simultaneously at the Hip and Knee,* D. Bourbonnais et al., J. Biomechanics, vol. 26, No. 3, pp. 277–283, 1993.

Primary Examiner—Jeanne M. Clark
Attorney, Agent, or Firm—Bell, Seltzer, Park & Gibson, P.A.

[57] ABSTRACT

An apparatus for measuring the strength of and for performing physical therapy exercises to strengthen a patient's limb. The device includes a pair of pivot clamps each having a end for connecting the pivot clamps to a solid object such as a physical therapy table or hospital bed. A second end of each pivot clamp adjustably receives a first frame member of a conventional traction or load frame. This arrangement enables rotational and translational movement of the first frame member retained by the pivot clamp relative to each pivot clamp to allow the frame to be positioned in a desired location and orientation relative to the patient's limb to be tested. A second frame member is adjustably connected to the pair of first frame members by a pair of adjustable brackets. A limb engaging member having a force transducer located therein is used to both engage the patient's limb to be tested and to detect a force transmitted between the limb of a patient and the limb engaging member. The force transducer produces an output which is representative of the force produced which may be displayed on a digital panel meter.

32 Claims, 4 Drawing Sheets

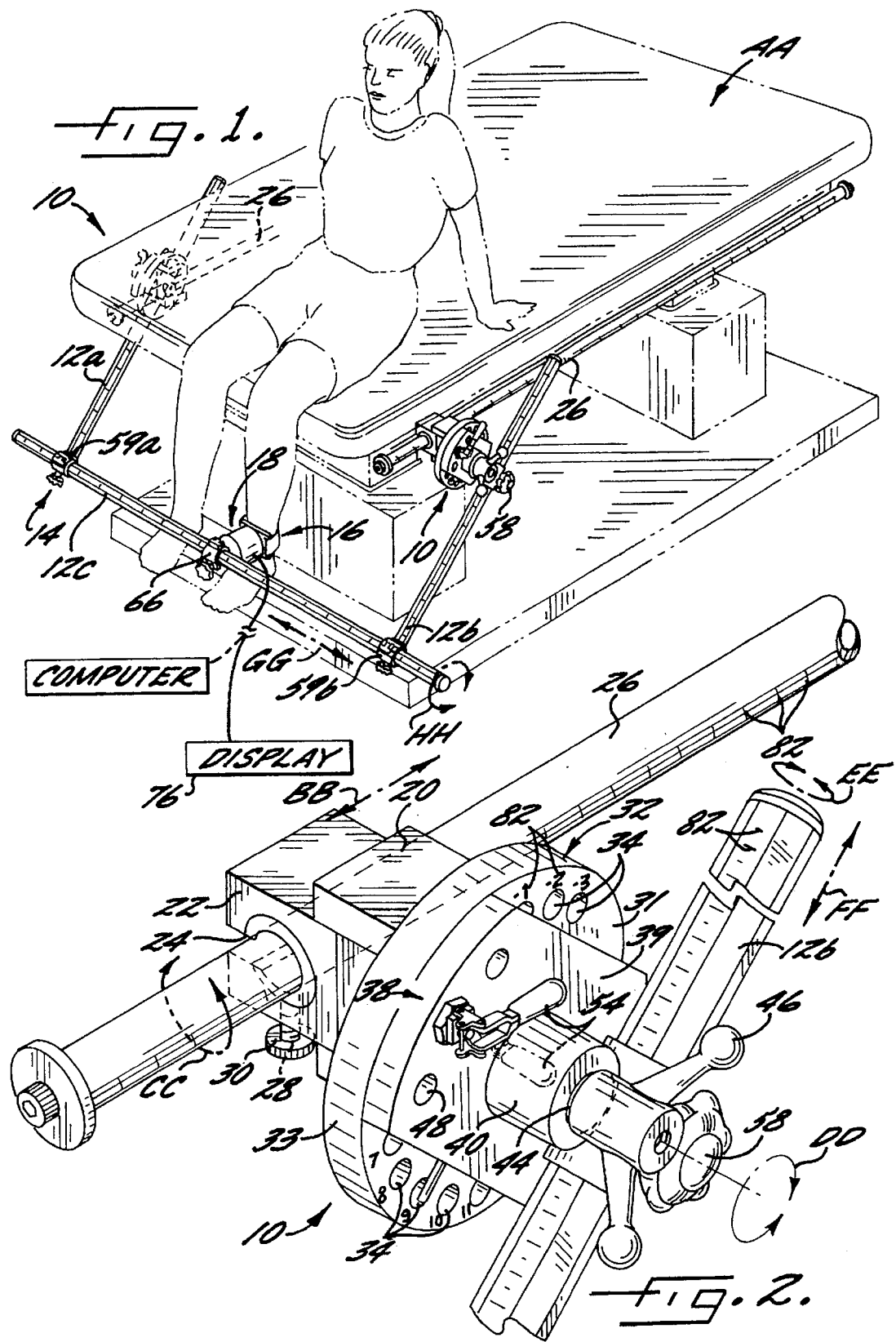

TO DISPLAY

APPARATUS FOR EXERCISING AND MEASURING STRENGTH OF A PATIENT'S LIMB AND AN ADJUSTABLE PIVOT CLAMP

FIELD OF THE INVENTION

The present invention relates to the field of muscle physical therapy and strength measuring devices, and, more particularly, to an apparatus and method for measuring the strength of and for performing physical therapy exercises to strengthen a patient's limb.

BACKGROUND OF THE INVENTION

It has long been recognized as beneficial to patient recovery that exercise or physical therapy begin as soon as possible after an operation to replace or repair an injured joint or limb. It has traditionally been popular to use a conventional orthopedic traction frame similar to that disclosed in U.S. Pat. No. 4,551,872 to Reed to assist a patient in performing remedial exercises. For example, U.S. Pat. No. 3,612,042 to Fry uses a fixed traction frame and adds a number of attachments, such as a swivel assembly and a series of members, to allow a patient to passively exercise his hip while remaining in the hospital bed.

Similarly, U.S. Pat. No. 4,602,618 to Berze discloses the use of a continuous hip-joint motion machine which is attached to a hospital bed. The machine also uses a fixed traction frame to support a series of pulleys which cooperate with the machine to passively exercise the hip joint after replacement surgery.

U.S. Pat. No. 2,855,199 to Noland et al., discloses a progressive resistance device which is removably mounted to a table for exercising both the hamstring and quadriceps femoris muscle groups.

In addition to exercising or rehabilitating injured joints or limbs, it is also important for physicians, physical therapists and exercise physiologists to be able to quantitatively measure and test the strength of a patient's joint or limb prior to, and as a result of exercise and/or surgery. Typically, such testing methods include the use of hand-held dynamometers. For instance, an article by Bohannn entitled *Knee Extension Torque In Stroke Patients: Comparison of Measurements Obtained With A Hand-Held Dynamometer ("HHD") And A Cybex Dynamometer* discloses the difficulty a tester has in holding a HHD steady during testing of knee extension, if the patient comes to maximal force immediately. In addition, the article discloses the importance of the tester's strength and skill in obtaining accurate measurements.

Rather than using a hand-held dynamometer, complicated devices such as U.S. Pat. No. 5,078,152 to Bond et al. have been developed. The Bond et al. patent discloses a method for diagnosis and/or training of proprioceptor feedback in a muscle and joint system of a human patient. The device is a stand alone unit which includes a passive exercise resistance system having a force measuring system and a position measuring system to determine exercise parameters and feed signals to a computer control system which runs a software program to control the exercise to be performed by a patient. Similarly, U.S. Pat. No. 3,374,675 to Keropian discloses an isometric muscle testing apparatus which requires a slide-block to attach a complicated arrangement of a support bar, a tubular channel support member, a positioning bar, a lockable hinge brake, a measuring arm, a split sleeve, and a load cell assembly to a table. This arrangement is unstable and subject to inaccurate results because of the inherent flexing of the apparatus and the torsional force applied to the load cell assembly during testing, due to the number of interconnected bars and rods secured to the table by the slide-block.

Load or traction frames currently available are limited in their ability to be adjusted to accommodate exercise equipment. Specifically, existing traction frames do not possess the structure necessary to allow it to be pivoted about a horizontal axis relative to the hospital bed or physical therapy table. As a result, there are only a finite number of adjustments which can be made to position the traction frame and the associated exercise equipment relative to the patient. Consequently, patients are unable to take full advantage of the benefits of exercise while recovering in a hospital bed.

The ability to test limb strength of a patient is an important indicator of a variety of factors, such as pre-operation versus post-operation strength. It is therefore desirable to obtain the most reliable quantitative results possible. Existing testing methods use either hand-held dynamometers, which are heavily dependant on the strength and ability of the tester or a machine such as a Cybex dynamometer, requiring a patient to be moved from a hospital bed for testing. In addition, such machines compete for limited hospital budgets because of their associated cost. Consequently, hospitals are faced with a choice between using expensive equipment to conduct their tests of patients or rely on a hand dynamometer which makes quantifiable results in repeated tests difficult to achieve.

SUMMARY OF THE INVENTION

In view of the foregoing background, it is therefore an object of the invention to provide an apparatus and an associated method for measuring the strength of and rehabilitating a patient's limb.

These and other objects, features, and advantages of the invention are provided by a pair of pivot clamps each having a first end for connecting each of the pivot clamps to a solid object such as a physical therapy table or hospital bed. A second end of each pivot clamp adjustably receives a first frame member of a conventional traction or load frame. The load frame also includes a second frame member which spans the distance between and is connected to the pair of first frame members by a pair of adjustable brackets. Such an arrangement enables the load frame retained by the pivot clamps to move longitudinally and rotate relative to each pivot clamp to allow the load frame to be positioned in a desired location relative to the patient's limb.

The pair of first frame members and the second frame number cooperate with the pair of pivot clamps to provide a rigid structure or frame which partially surrounds the physical therapy table or the hospital bed to enable the rigid frame to be positioned in a plurality of locations relative to the patient's limb. Alternatively, rather than provide a rigid frame, it is possible to use only one pivot clamp, which retains one first frame member and an adjustable bracket to adjustably connect a second frame member to the first frame member such that the second frame member is oriented generally traverse to the first frame member. Preferably, the second frame member is slidably and rotatably adjustable relative to the first frame member to position the limb engagement means in a desired location relative to the limb to be measured.

It is also beneficial to provide a limb engaging member which can be adjustably connected to at least one of the frame members and be movable therewith to engage the patient's limb in the desired location during measurement thereof. A force transducer is preferably connected to the limb engaging member to detect a force transmitted between the limb engaging member and the limb of the patient. The force transducer preferably produces an output which is representative of the force produced between the patient's limb and the limb engaging member. This representative output is capable of being displayed on a display means such as a digital panel meter.

It is advantageous for the force transducer to include a housing which defines a cavity for receiving therein a strain gauge which cooperates with the limb engaging member. The limb engaging member preferably includes a retaining strap which releasably attaches to and securely retains the patient's limb to be measured in such a manner that it allows for measuring of both compression and tensile strength of the patient's limb.

To enhance the ability to position the limb engaging member relative to the patient, it is beneficial for a slide rail to be attached to one or both sides of the physical therapy table. In connection therewith, a first end of the pivot clamp preferably includes an adjustable bracket which enables translational movement of the pivot clamp relative to the slide rail for positioning the pivot clamp and the frame member along a horizontal path relative to the patient positioned on the physical therapy table. This configuration also allows for rotational movement of the pivot clamp and the frame member about the longitudinal axis of the slide rail relative to the patient and the table.

In addition, indexing means is preferably provided on both the pivot clamp, the frame members, and when used, the slide rail to allow the patient's limb, the rigid frame, and the limb engaging member to be readily positioned in the same location on subsequent tests.

An alternative use of the apparatus is for purposes of exercising and rehabilitating a patient's limb. As previously described, the rigid frame is formed from a pair of first frame members adjustably attached by a pair of brackets to a second frame member, enabling each of the frame members to move relative one another. Both translational and rotational movement of the frame members is possible.

The rigid frame is secured by a pair of pivot clamps to the physical therapy table or the like. The pivot clamps enable each of the pair of first frame members received therein, to pivot relative to the physical therapy table and undergo translational and rotational movement relative to each of the pivot clamps so as to enable the rigid frame to be positioned in the desired location and orientation relative to the patient.

In addition, as with the testing apparatus previously described, it is beneficial to provide a pair of slide rails along the longitudinal edges of the physical therapy table to enable rotational and translational movement of the rigid frame relative to the patient, thereby enhancing the ability to position the rigid frame in the desired location.

A plurality of exercise apparatuses are preferably adapted to be received on the rigid frame to enable the patient to exercise and rehabilitate the desired body part. In addition, it is possible to attach more than one rigid frame to the physical therapy table in order that the two rigid frames may cooperate to receive a more complicated exercise apparatus for exercising and rehabilitating the desired body part. The ability of the rigid frame and the pivot clamp to undergo pivotal, translational and rotational movement relative to each other and relative to the hospital bed or physical therapy table allows infinite variability of the device.

BRIEF DESCRIPTION OF THE DRAWINGS

Some of the objects and advantages of the present invention have been stated, others will appear as the description proceeds, when taken in conjunction with the accompanying drawings in which;

FIG. 1 is a side view in perspective of the apparatus during performance of an isokinetic assessment of a patient's limb in accordance with the present invention;

FIG. 2 is a side view in perspective, partially in phantom, of the pivot clamp shown in FIG. 1;

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In the embodiment shown in FIGS. 1–6 and 8, the device includes a pair of pivot clamps 10 which are capable of being attached to either a physical therapy table or the like, generally designated as AA, or to a solid object such as a wall, door or the like (not shown). The pivot clamps 10 each cooperate with a plurality of frame members 12a–12c to form a rigid frame, generally designated as 14. In this embodiment, the frame members 12a–12c are conventional load or traction frame components which are readily available at most hospitals and physical therapy centers. A limb engaging member 16 releasably connects at one end thereof to the rigid frame 14 and at its opposite end to a patient's limb to be measured. A force transducer, generally designated at 18, is connected to the limb engaging member 16 for detecting a force transmitted between the patient's limb and the limb engaging member.

Figure 3:
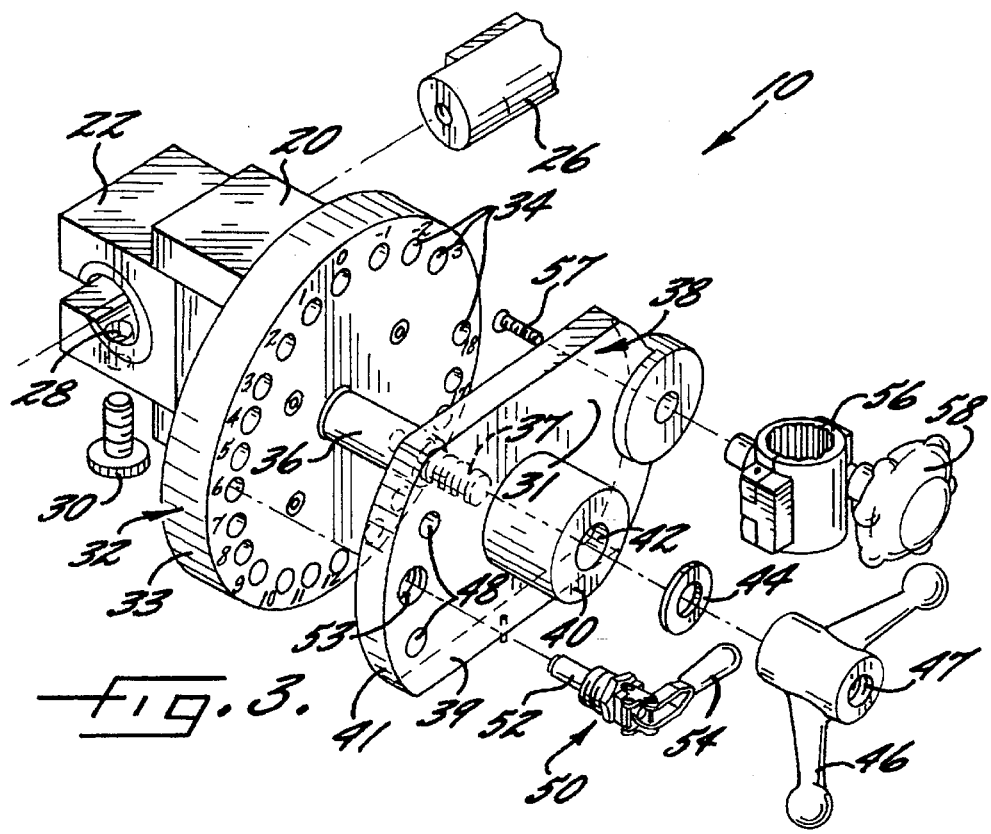
FIG. 3 is an exploded view of the pivot clamp shown in FIG. 2.
Figure 4:
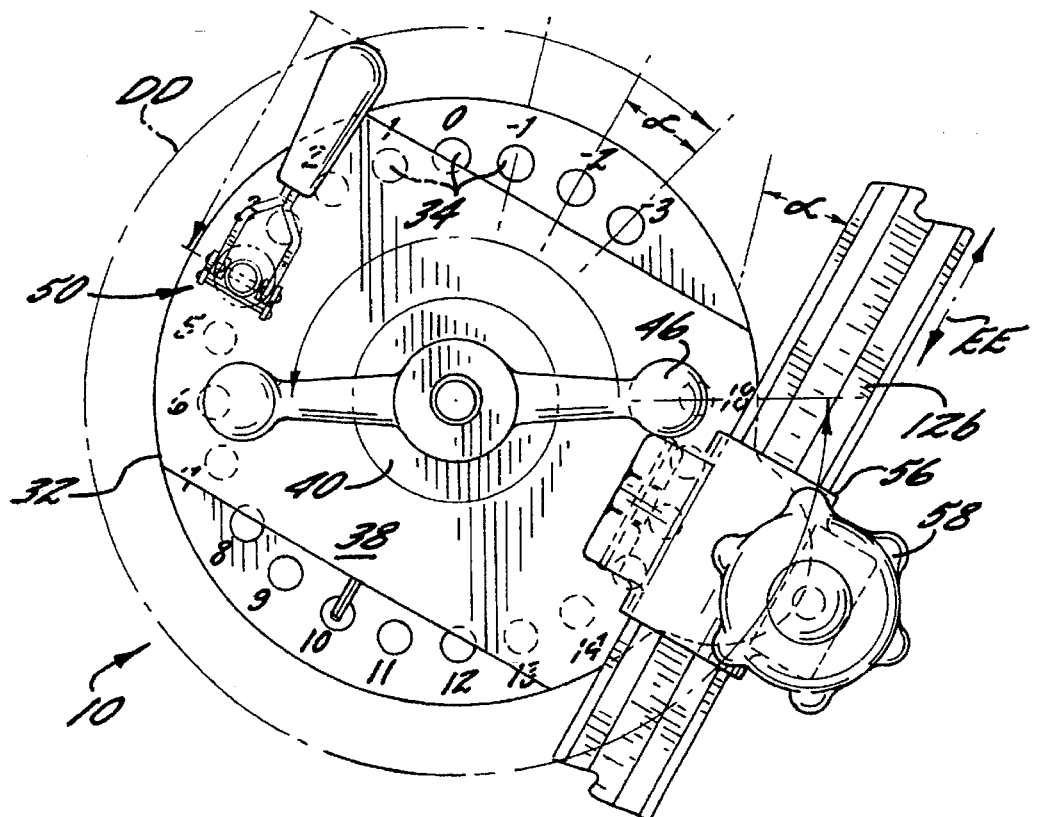
FIG. 4 is an end view of the pivot clamp shown in FIGS. 2 and 3.

As shown in detail in FIGS. 2–4, each of the pivot clamps 10 includes a body portion 20 having a first end 22 which, in the embodiment shown, defines a first key-hole shaped opening 24 adapted to receive a slide bar 26 fastened to the physical therapy table AA. It is to be understood however that first end 22 may be a mounting plate (not shown) to fixedly attach each of the pivot clamps 10 to the physical therapy table AA or a fixed object such as a wall.

A second opening 28 in the body 20 is oriented generally transverse to the first opening 24 for threadingly receiving an adjustable retaining screw 30. The retaining screw 30, when loosened, selectively allows both translational and rotational movement of each pivot clamp 10 on the slide rail 26 in the direction of arrows BB and CC, respectively, as shown in FIG. 2, to the desired position and orientation relative to the patient located on the physical therapy table AA. The retaining screw 30 is then tightened to secure the pivot clamp 10 into position.

A first plate 32 is integrally formed with the body portion 20. The first plate 32 has a generally circular configuration with a substantially smooth front face 31 and peripheral edge 33 and is oriented generally transverse to the longitudinal axis of the body portion 20. A plurality of first apertures 34 are located along the peripheral edge 33 of the front face 31 of the first face plate 32. The plurality of first apertures 34 are spaced apart in ten degree intervals around the entire first face plate 32. It is to be understood however that the intervals between the plurality of first apertures 34 may vary as desired. Centrally located in the first face plate 32 and extending generally transverse thereto, is a shaft 36 having a threaded free-end 37.

A second end of the pivot clamp 10 comprises a second face plate 38 having a substantially smooth front face 39. The second face plate 38 includes a mounting collar 40. The mounting collar 40 defines a bore 42 sized to receive the shaft 36. The collar 40 is adapted to be seated on the shaft 36 enabling the threaded free end 37 of the shaft to project outward therefrom. The second face place 38 has a generally rectangular configuration with a pair of opposed substantially smooth curved peripheral ends 41 which correspond in shape and size to the peripheral edge 33 of the first face plate 32. A plurality of second apertures 48 are located along the curved peripheral edge of the second face plate 38. The second apertures 48 may be spaced at a distance similar to that of the first apertures 34. Alternatively, it is possible to space the second apertures 48 a distance which is either greater or less than that of the first apertures 34.

After the second face plate 38 is seated on the shaft adjacent the first face plate 32, a washer 44 is fitted onto the threaded free-end 37 of the shaft 36. A tightening means, which in this embodiment is a wing nut handle 46 having an internal threaded bore 47 is then threaded onto the shaft 36 so as to selectively lock the second face plate 38 relative to the first face plate 32, once the second face plate 38 has been rotated to the desired position. It is to be understood that a wide variety of tightening means may be used, such as a nut or other conventional fastener and remain within the spirit of the invention.

Figure 7:
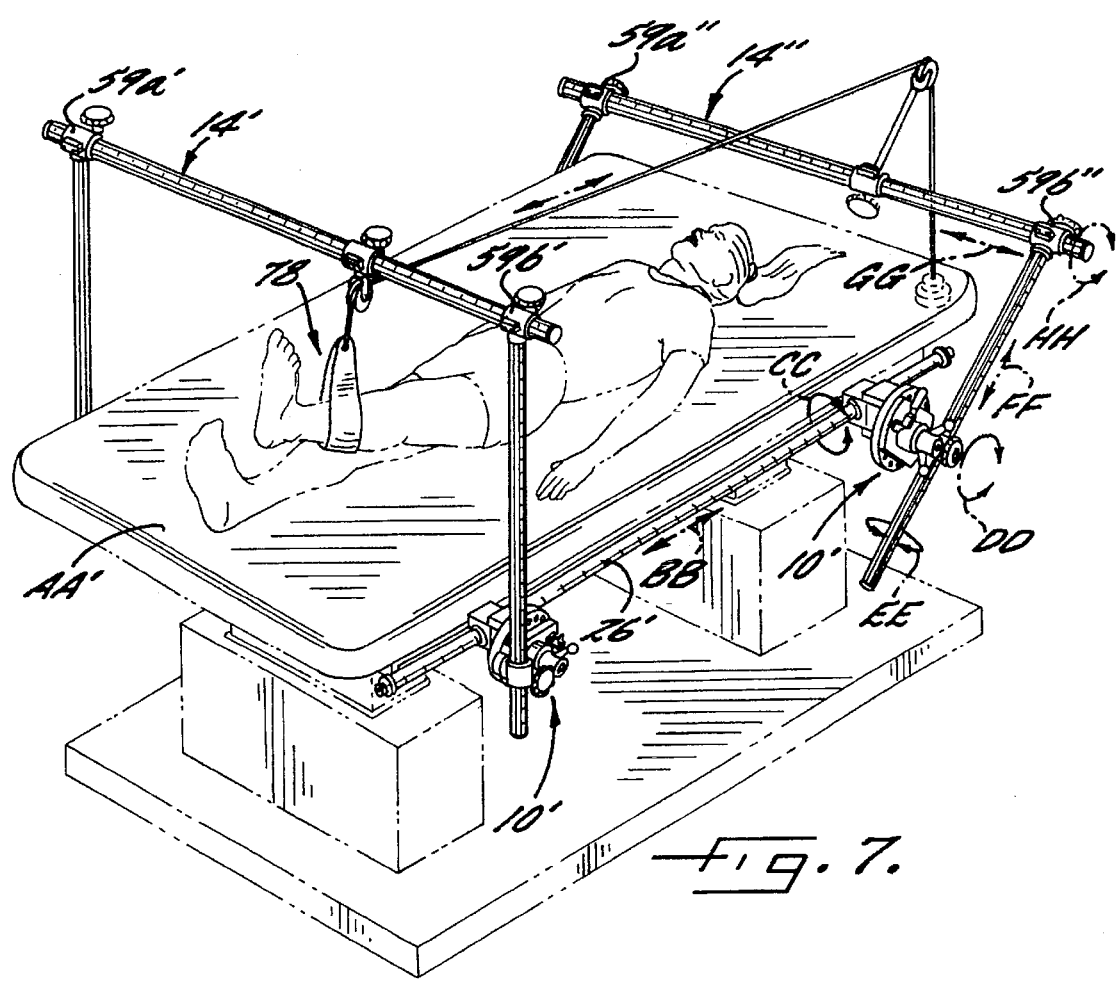
FIG. 7 is a side view in perspective of the apparatus during the performance of physical therapy in accordance with the present invention.

A release pin, in this embodiment a quick release pin generally indicated at 50, is secured to the front face 39 of the second face plate 38 such that a pin portion 52 is received in a mounting aperture 53. The handle 54 of the quick release pin 50 is movable between a first position (shown in phantom in FIG. 2) and a second position (shown in FIG. 4). In the first position, the handle 54 is in general longitudinal alignment with the pin portion 52, which causes the pin portion to be retracted toward the handle so that the pin portion does not project beyond the second face plate 38. The retraction of the pin portion 52 from the first apertures 34 enables pivotal movement of the second face plate 38 relative to the first face plate 32 in the direction of arrow DD as shown in FIGS. 2, 4, and 7.

To allow the second face plate 38 to pivot in the first position, it is also necessary for the wing nut handle 46 to be loosened about the shaft 36. When the second face plate 38 has been pivoted to the desired position relative to the first face plate 32, the mounting aperture 53 aligns with one of the plurality of first apertures 34. The handle 54 of the quick release pin 50 is then moved to the second position wherein the pin portion 52 projects or is inserted into the aligned first aperture 34 of the first face plate 32. The wing nut handle 46 is then tightened in a generally clockwise direction to lock the second face plate 38 relative to the first face plate 32. The second apertures 48 are located on either side of the mounting aperture 53 to assist in aligning the mounting aperture with one of the first apertures 34.

The front face 39 of the second face plate 38 also has a first adjustable bracket 56 secured thereto by conventional means such as a screw 57. The first adjustable bracket 56 is adjustable by means of a bracket handle 58 which alternatively loosens and tightens the adjustable bracket so as to receive one of the first frame members 12a or 12b. As shown in FIGS. 2 and 4, the first adjustable bracket 56 is adapted to receive the first frame member 12b. In this embodiment, the rigid frame 14 is formed from frame members 12a–12c having a generally octagonal cross-section which enables both rotational movement about the longitudinal axis of the respective first frame members 12a and 12b in the direction of arrow EE and translational movement of the respective frame members relative to the pivot clamp 10 in the direction of arrow FF shown in FIGS. 2 and 4 when the first adjustable bracket 56 is loose.

Based upon the ability of the second face plate 38 to also pivot relative to the first face plate 32 in the direction of arrow DD, the rigid frame 14 may be pivoted horizontally relative to the physical therapy table AA. The second frame member 12c is also adjustably attached to the first frame members 12a and 12b by a pair of second adjustable brackets 59a and 59b. The second adjustable brackets 59a, 59b allow translational movement of the second frame member 12c relative to the pair of first frame members 12a, 12b in the direction of arrow GG to move it closer or further from the table AA and rotational movement of the second frame member about its longitudinal axis in the direction of arrow HH in FIG. 1. Accordingly, the rigid frame 14 may be infinitely adjusted about any or all of the described three degrees freedom in order to position the limb engaging member 16 in the desired location and orientation relative to the patient's limb to be measured.

Figure 5:
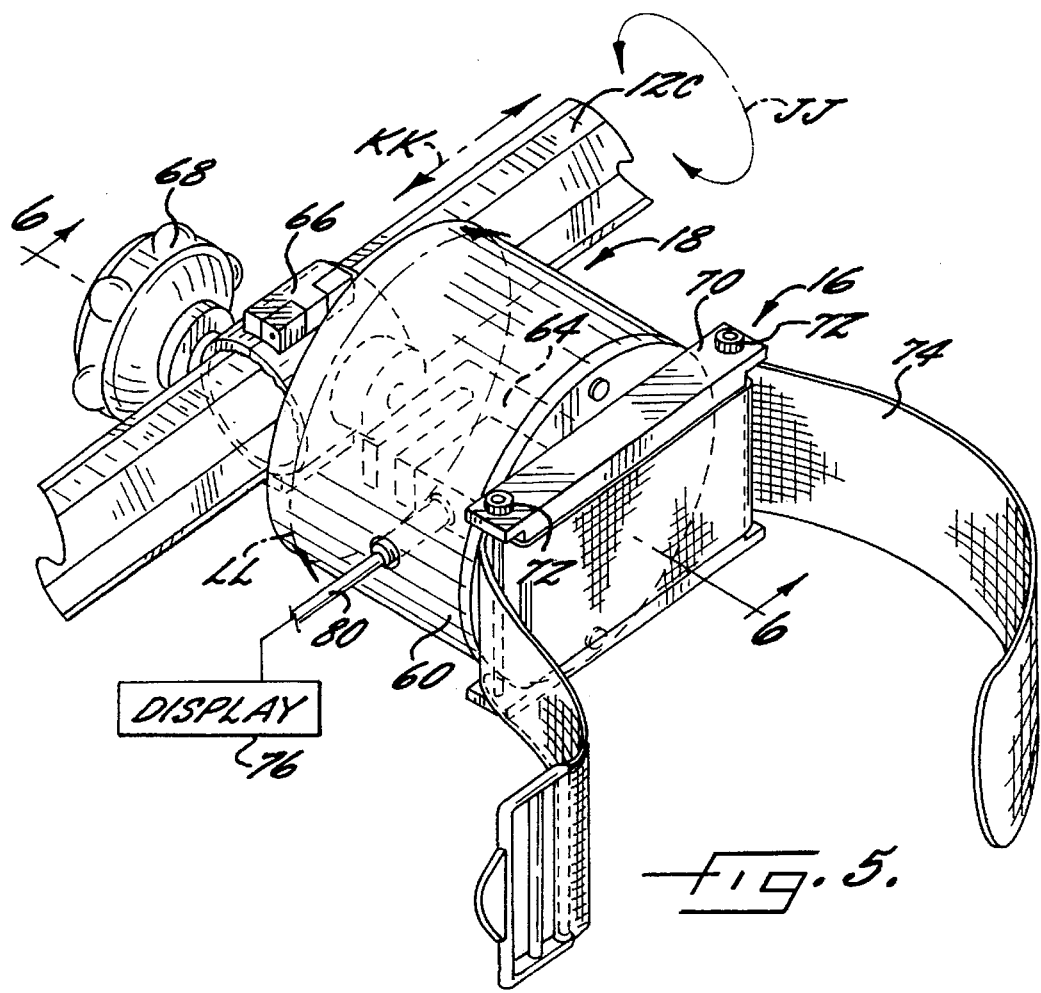
FIG. 5 is a side view in perspective of the limb engagement means shown in FIG. 1.
Figure 6:
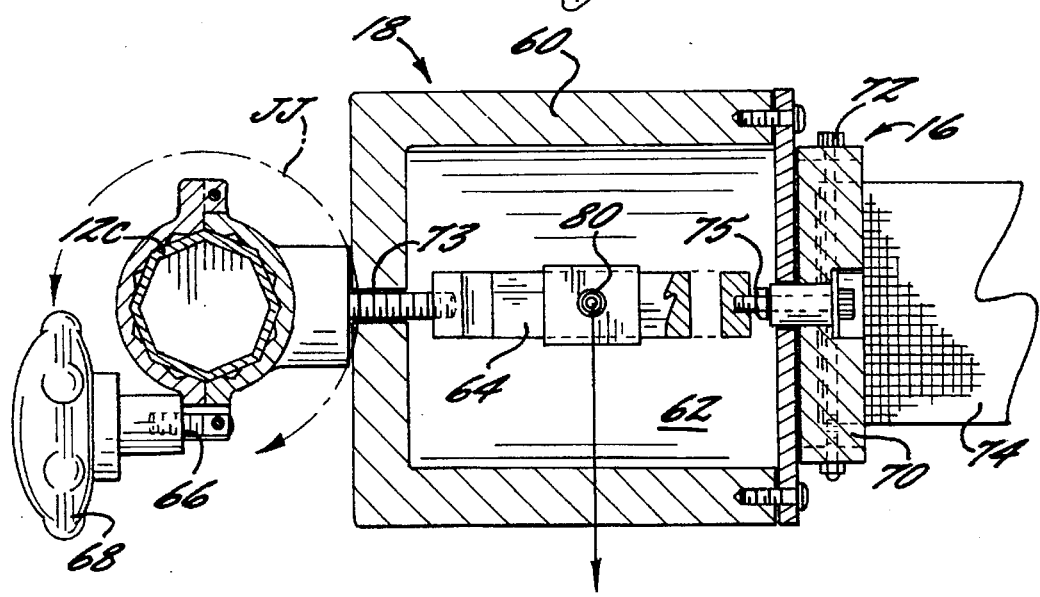
FIG. 6 is a side view in cross-section taken along line 6—6 of FIG. 5.
Figure 8:
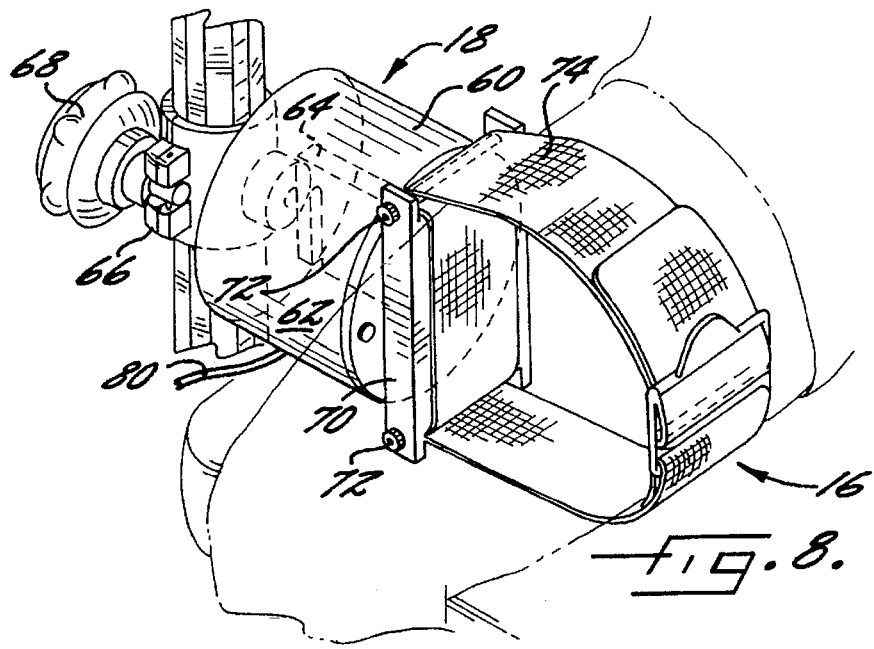
FIG. 8 is a perspective view of the limb engagement means showing the retaining strap securing a patient's limb during the performance of a isokinetic assessment of the limb in accordance with the present invention.

As shown in FIGS. 5, 6, and 8, the force transducer 18 includes a housing 60 having a generally cylindrical configuration. The housing 60 defines an internal cavity 62 for receiving therein a strain gauge 64 oriented so as to cooperate with the limb engaging member 16. The housing 60 of the force transducer 18 is connected at one end thereof to a third adjustable bracket 66 having a configuration similar to the first and second adjustable brackets 56 and 59a, 59b. A third adjustable bracket handle 68 enables the force transducer 18 to be connected to one of the first pair of frame members 12a and 12b or the second frame member 12c as well as enable rotational movement relative to the longitudinal axis of the respective frame member in this instance 12c in the direction of arrow JJ in FIGS. 5 and 6 and allow translational movement relative to the third adjustable bracket in the direction of arrow KK in FIG. 5.

The limb engaging member 16 is pivotally connected to the housing 60 by means of a mounting member 70. The mounting member 70, as shown in FIGS. 5 and 8, is a generally rectangular plate having guides 72 located at opposed ends thereof for receiving a retaining strap 74. In this embodiment, the retaining strap has a buckle and loop arrangement which allows the retaining step 74 to be releasably secured around a patient's leg to ensure that there is no play between the limb engaging member 16 and the patient's leg. It is to be understood that alternative forms of the retaining strap 74 may be used as long as the retaining strap 74 easily opens and closes to alternatively release and secure a patient's leg and secondly has a fastening device which is sufficiently secure to retain the patient's leg to avoid any excessive movement between the patient's limb and the limb engaging member.

As may be seen in FIGS. 5, 6, and 8, the strain gauge 64 is oriented along the longitudinal axis of the housing 60. The strain gauge 64 is threadingly secured at one end thereof by a threaded bolt 73 extending outward therefrom, to the second adjustable bracket 66. The opposed end of the strain gauge 64 is secured by a threaded nut and bolt, collectively referred to as 75, which allows pivotal movement of the mounting member 70 relative to the housing 60 in direction LL as shown in FIG. 5. This arrangement also enables the strain gauge 64 to form a solid attachment between the frame member, in this embodiment, second frame member 12c, and the mounting member 70 of the limb engaging member 16, to ensure that any tensile or compression force exerted by the patient's limb is directly transferred to the strain gauge. The strain gauge 64 of the force transducer 18 produces an output which is representative of the directed force applied by the patient's limb and transfers this output to a display 76. A digital panel meter may be used for displaying the output received from the force transducer 18 in digital form.

The operation of the device will now be disclosed to better enhance the understanding of the present invention. A patient is positioned on the physical therapy table AA in a desired location, in this instance, sitting on the edge of the table with both legs hanging over the edge thereof. The rigid frame 14 is then moved from a storage position (not shown). The retaining screw 30 of each of the pair of pivot clamps 10 is loosened to enable translational movement BB of each of the pivot clamps along the slide rail 26 toward the end of the table AA adjacent the patient. Once the pivot clamps 10 have been moved adjacent the patient, in the desired location, the retaining screw 30 of each of the pivot clamps is tightened to prevent further sliding of the pivot clamps. The handle 54 of the quick release pin 50 is then moved to the first position retracting pin portion 54 from the aligned first aperture 34 of the first face plate 32 and the wing nut handle 46 is then rotated in a counterclockwise direction to loosen the handle relative to the shaft 36 of the first face plate 32.

The second face plate 38 of each pivot clamp, taking the rigid frame 14 with it, is then pivoted downward in the direction of arrow DD to the desired location, in this instance adjacent the floor, as shown in FIG. 1. Once in the desired location, the handle 54 of the quick release pin 50 is moved to the second position causing the pin portion 52 to project passed the second face plate 38 and into the aligned aperture 34. The wing nut handle 46 is then rotated in the clockwise direction to tighten down the second face plate 38 relative to the first face plate 34. If necessary, the handle 58 of the first adjustable bracket 56 is loosened to allow the first frame members 12a and 12b to translate longitudinally in the direction of arrow FF relative to the pivot clamp 10 and move second frame member 12c either closer to or further from the patient seated upon the physical therapy table AA. The handle 58 is rotated in a clockwise direction to tighten the adjustable bracket 56 about the first frame members 12a and 12b once the desired location has been achieved. It is to be understood that adjustments about all the available degrees of freedom need not be made to position the rigid frame 14 in the desired position and orientation for each test. However, the ability to move the rigid frame and pivot clamps in such a multitude of degrees of freedom relative to the patient and the table greatly enhances the versatility of the device.

The limb engaging member 18 is then positioned laterally, i.e., undergoes translational movement, in the direction of arrow KK relative to and/or rotated about the second frame member 12c in the direction of arrow JJ by loosening the third adjustable bracket 66. The force transducer 18 and the limb engaging member 16 should be positioned so as to properly align with the limb of the patient to be measured. The retaining strap 74 of the limb engaging member 16 is then comfortably secured about the patient's limb to be measured.

Upon direction from the individual conducting the test, the patient either flexes or extends the limb to exert either a compression or tensile force, respectively against the limb engaging member 16. The pressure exerted by the patient against the limb engaging member 16 is transferred to the force transducer 18. The measured force exerted by the patient is carried by a cable 80 to the output display device 76 where it is displayed in a desired form, in this case as a digital readout.

Each of the pair of first frame members 12a, 12b, the second frame member 12c, the first face plate 32 and, when used, the slide rail 26 have index markings 82 along a surface thereof to enable the pivot clamp 10, the limb engaging member 16, and the rigid frame 14 to be easily repeatably positioned in the same location for subsequent tests to ensure uniformity and reliability of such tests.

An alternative embodiment of the device is shown in FIG. 7. In this embodiment, the device is intended for use in exercising or conducting physical therapy of a patient's joint or limb. It is anticipated, that the device will be used with a patient on a physical therapy table or hospital bed designated AA'.

In this alternative embodiment, the pivot clamps 10' are used with a rigid frame 14' similar to the one previously described. A variety of exercise equipment may be attached to the rigid frame by use of attachment means such as the third adjustable bracket described above. In addition, a second rigid frame 14" may be used in conjunction with the first rigid frame 14' to cooperatively receive a variety of exercise equipment such as the weight and sling shown generally at 78. It is to be understood that the rigid frame 14' and the pivot clamps 10' are identical to those previously discussed in the context of the preferred embodiment shown in FIGS. 1–6 and 8. The ability of the pivot clamps 10' and the rigid frames 14' and 14" to selectively move about the numerous of degrees of freedom allows the rigid frame 14' to be adjusted in an infinite variety of positions with a wide variety of exercise equipment. For example, rather than using the pair of first frame members 12a and 12b, and the second frame member 12c to form a generally rectangular rigid frame 14, it is possible, within the spirit of this invention, to use only the two first frame members and an adjustable bracket such as second adjustable bracket 59a, and rotate the pivot clamps 10 about the slide rails 26 in the direction of arrow CC to create a triangular load frame (not shown) or a variety of other configurations.

In the drawings and specification, there have been disclosed typical preferred embodiments of the invention and, although specific terms are employed, they are used in a generic and descriptive sense only and not for purposes of limitation, the scope of the invention being set forth in the following amended claims.

That which is claimed:

1. An apparatus adapted for use in exercising and measuring strength of a patient's leg, said apparatus comprising:

a slide rail;

a frame member;

a pivot clamp having a first plate defining an opening in a first end, said first end also including a clamping mechanism for connecting the first plate in a desired location and orientation to said slide rail and said pivot clamp having a second plate connected to said first plate and selectively rotatable relative thereto, said second plate having a second end for connecting said frame member in a desired location and orientation relative to the patient's limb, wherein said pivot clamp provides selected rotational and translational movement between said slide rail and said frame member;

a limb engaging member connected to said frame member and movable therewith and adapted for engaging the patient's limb; and a force transducer connected to said limb engaging member for detecting a force transmitted between said limb engaging member and the patient's limb, said force transducer producing an output representative of the detected force.

2. An apparatus according to claim 1 wherein said second plate is in releasable frictional engagement with said first plate.

3. An apparatus according to claim 2 further comprising locking means for locking said second plate relative to said first plate when said second plate is in the desired location.

4. An apparatus according to claim 3 wherein said locking means comprises a threaded shaft extending outward from said first plate and tightening means threadingly cooperating therewith for locking said second plate to said first plate in the desired position.

5. An apparatus according to claim 2 further comprising locating means for rotationally locating said second plate relative to said first plate.

6. An apparatus according to claim 5 wherein said locating means comprises a plurality of spaced first apertures located in said first plate and a plurality of spaced second apertures located in said second plate so as to selectively align with said first apertures, and a release pin insertable in one of said first apertures and one of said second apertures to position said second plate relative to said first plate.

7. An apparatus according to claim 6 wherein said release pin is connected to said second plate.

8. An apparatus according to claim 7 wherein said plurality of second apertures are fewer in number than said plurality of first apertures.

9. An apparatus according to claim 1 wherein said pivot clamp further comprises a first adjustable bracket attached to said second end to enable said frame member rotational and translational movement relative said pivot clamp to thereby enhance the positioning and orientation of said frame member relative to the patient.

10. An apparatus according to claim 1 further comprising a second adjustable bracket for adjustably connecting a second frame member to said frame member, such that said second frame member is oriented generally transverse to said frame member, and enabling said second frame member translational and rotational movement relative to said frame member for positioning said limb engaging member in a desired location and orientation relative to the limb to be measured.

11. An apparatus according to claim 1 wherein said force transducer comprises:

a housing;

a bracket attached to said housing for connecting said housing to said frame member for positioning said housing in the desired location; and a strain gauge connected to said housing and oriented to cooperate with said limb engaging member.

12. The apparatus according to claim 11 wherein said limb engaging member comprises a mounting member pivotally connected to said housing and a retaining strap adapted for releasably attaching to and retaining the patient's limb.

13. An apparatus according to claim 11 wherein said force transducer selectively measures both compression and tensile force applied to said engaging means.

14. An apparatus according to claim 1 further comprising a display for displaying said output.

15. An apparatus according to claim 14 wherein said display comprises means for converting said output received from said force transducer to a digital representation.

16. An apparatus according to claim 1 wherein said frame member comprises indexing means located along a surface thereof enabling said limb engaging member to be repeatedly positioned in the desired location relative to said pivot clamp and the patient's limb.

17. An apparatus according to claim 1 wherein said pivot clamp includes indexing means located along a surface thereof enabling said pivot clamp and said frame member to be repeatedly positioned relative to the patient's limb.

18. An apparatus adapted for use with a table and a load frame having a pair of first opposed frame members and a second frame member attached generally transverse to the pair of first frame members, said apparatus comprising:

a pair of slide rails adapted to be connected to the table;

a pair of pivot clamps, each of said pair of pivot clamps having a first plate defining an opening in a first end, each said first end also including a clamping mechanism for connecting each said first plate in a desired location and orientation to a respective one of said pair of slide rails, and each of said pair of pivot clamps having a second plate rotatably connected about a generally horizontal axis to said first plate, said second plate having a first adjustable bracket attached at a second end thereof adapted for connecting said first opposed frame members in a desired location relative to the patient's limb, wherein said pair of pivot clamps each provides selected rotational and translational movement between the table and said first opposed frame members;

a limb engaging member adapted to be connected to the load frame and movable therewith for engaging the patient's limb in the desired location; and a force transducer connected to said limb engaging member for detecting a force transmitted between said limb engaging member and the patient's limb, said force transducer producing an output representative of the force detected between the patient's limb and said limb engaging member.

19. An apparatus according to claim 18 wherein each of said pivot clamps further comprises:

locating means for locating said second plate relative to said first plate; and locking means for locking said second plate relative to said first plate when said second plate is positioned in the desired location.

20. An apparatus according to claim 18 wherein said force transducer comprises:

a housing defining a cavity;

a third adjustable bracket for connecting said housing to the load frame for positioning said housing in the desired location; and a strain gauge received within said cavity and oriented so as to cooperate with said limb engaging member.

21. The apparatus as defined in claim 20 wherein said limb engaging member comprises a mounting member pivotally connected to said housing and a retaining strap adapted for attaching to and retaining the patient's limb to be measured.

22. An apparatus according to claim 20 wherein said force transducer selectively measures both compression and tensile strength applied to said engaging means.

23. An apparatus according to claim 18 further comprising a digital panel meter for displaying said output received from said force transducer in digital form.

24. A pivot clamp for use with a rigid frame and a physical therapy table, said pivot clamp comprising a body portion having a first end, said first end also including a clamping mechanism for providing said pivot clamp rotational and translational movement relative to the physical therapy table;

a first plate connected to said body portion generally transverse to a longitudinal axis thereof, said first plate having substantially smooth opposed faces;

a second plate connected for rotational movement with respect to said first plate and having a substantially smooth face in releasable frictional engagement with said first plate;

locating means for rotationally locating said second plate relative to said first plate;

locking means for locking said second plate relative to said first plate when said second plate is positioned in the desired location; and a first adjustable bracket connected to said second plate and movable therewith and adapted for receiving the rigid frame to allow translational and rotational movement relative to said adjustable bracket, and said first adjustable bracket enabling said second plate and the rigid frame received therein to pivot relative to the table and said first plate so as to position the rigid frame in a desired location and orientation.

25. An apparatus according to claim 24 wherein said locking means comprises a threaded shaft extending outward from said first plate and tightening means threadingly cooperating therewith for locking said second plate to said first plate in the desired position.

26. An apparatus according to claim 24 wherein said locating means comprises a plurality of spaced first apertures located in said first plate and a plurality of spaced second apertures located in said second plate so as to selectively align with said first apertures, and a release pin insertable in one of said first apertures and one of said second apertures to position said second plate relative to said first plate.

27. An apparatus according to claim 26 wherein said release pin is connected to said second plate.

28. An apparatus according to claim 27 wherein said plurality of second apertures are fewer in number than said plurality of first apertures.

29. An apparatus according to claim 24 wherein said first plate includes indexing means located along a surface thereof to allow said second plate to be repeatedly positioned relative thereto.

30. An apparatus according to claim 24 wherein said first plate has a generally circular configuration.

31. An apparatus according to claim 24 wherein said second plate has a generally rectangular configuration with a pair of curved opposed ends which correspond in shape to said first plate.

32. An apparatus according to claim 24 wherein said body portion and said first plate comprise a unitary one-piece structure.

\* \* \* \* \*

UNITED STATES PATENT AND TRADEMARK OFFICE
CERTIFICATE OF CORRECTION

PATENT NO. : 5,662,591
DATED : September 2, 1997
INVENTOR(S) : Peindl et al.

It is certified that error appears in the above-identified patent and that said Letters Patent is hereby corrected as shown below:

On the title page, item [56] should read:

In the References Cited, U.S. PATENT DOCUMENTS, line 14, "4,368,957" should read --4,368,997--; line 22, "Wagner, III" should read --Wagoner, III--.

Column 1, line 39, "Bohannn" should read --Bohannon--.

Column 2, line 47, "number" should read --member --.

Column 3, line 36, after "relative" insert --to--.

Column 7, line 47, "passed" should read --past--.

Column 8, line 44, after "numerous" cancel "of".

Column 1, after the title, insert:

--STATEMENT TO FEDERALLY SPONSORED RESEARCH

This invention was supported under NIH Grant Number R01 AR42659. The U.S. Government has certain rights to the invention.--.

Signed and Sealed this

Twenty-seventh Day of July, 1999

*Attest:*

Q. TODD DICKINSON

*Attesting Officer*  *Acting Commissioner of Patents and Trademarks*